US005656200A

United States Patent [19]

Boettcher et al.

[11] Patent Number: 5,656,200
[45] Date of Patent: Aug. 12, 1997

[54] FOAMING EMULSIONS

[75] Inventors: Axel Boettcher, Neuss; Hermann Hensen, Haan; Werner Seipel, Hilden; Holger Tesmann, Juechen, all of Germany

[73] Assignee: Henkel Kommanditgesellschaft auf Aktien, Duesseldorf, Germany

[21] Appl. No.: 495,690

[22] PCT Filed: Jan. 14, 1994

[86] PCT No.: PCT/EP94/00098

§ 371 Date: Jul. 24, 1995

§ 102(e) Date: Jul. 24, 1995

[87] PCT Pub. No.: WO94/16668

PCT Pub. Date: Aug. 4, 1994

[30] Foreign Application Priority Data

Jan. 23, 1993 [DE] Germany .................. 43 01 820.3

[51] Int. Cl.$^6$ .................................................. B01J 13/00
[52] U.S. Cl. .................... 252/307; 252/312; 252/314; 424/70.11; 424/70.19; 510/128; 510/135
[58] Field of Search ................... 252/307, 312, 252/174.17, 135, 314; 424/70.11, 70.19; 510/128, 135

[56] References Cited

U.S. PATENT DOCUMENTS

| 4,732,696 | 3/1988 | Urfer ........................ 252/174.17 |
| 4,824,594 | 4/1989 | Hoeffkes et al. ................. 510/135 |
| 4,898,690 | 2/1990 | Bitter et al. ..................... 510/135 |
| 5,100,573 | 3/1992 | Balzer ........................ 252/174.17 |
| 5,145,603 | 9/1992 | Paasch et al. ................... 252/311 |
| 5,374,716 | 12/1994 | Biermann et al. ................. 536/18.6 |
| 5,397,497 | 3/1995 | Jakobson et al. ................. 510/135 |
| 5,407,543 | 4/1995 | Miller ........................... 204/130 |
| 5,503,779 | 4/1996 | Adamy et al. ................. 252/174.17 |
| 5,534,248 | 7/1996 | Matsuo et al. ................... 424/70.19 |

FOREIGN PATENT DOCUMENTS

| 0070074 | 1/1983 | European Pat. Off. . |
| 0070075 | 1/1983 | European Pat. Off. . |
| 0070076 | 1/1983 | European Pat. Off. . |
| 0070077 | 1/1983 | European Pat. Off. . |
| 0301298 | 2/1989 | European Pat. Off. . |
| 0324451 | 7/1989 | European Pat. Off. . |
| 0337354 | 10/1989 | European Pat. Off. . |
| 0358216 | 3/1990 | European Pat. Off. . |
| 0384983 | 9/1990 | European Pat. Off. . |
| 0408965 | 1/1991 | European Pat. Off. . |
| 0409005 | 1/1991 | European Pat. Off. . |
| 0490041 | 6/1992 | European Pat. Off. . |
| 0510870 | 10/1992 | European Pat. Off. . |
| 3640755 | 6/1988 | Germany . |
| 4033928 | 4/1992 | Germany . |
| 4039950 | 6/1992 | Germany . |
| 4129926 | 7/1992 | Germany . |
| 4103489 | 8/1992 | Germany . |
| 4114141 | 11/1992 | Germany . |
| 9003977 | 4/1990 | WIPO . |
| 9201508 | 2/1992 | WIPO . |
| 9300417 | 1/1993 | WIPO . |
| 9406899 | 3/1994 | WIPO . |

OTHER PUBLICATIONS

Balzer, "Alkylpolyglycosides, Their Physico–Chemical Properties and Their Uses", Tens. Surf. Det. 28, 419 (1991) (month of references unknown).

D. Balzer, "Alkylpolyglycoside–Herstellung und Anwendung", Seifen–Oele–Fette–Wachse 118, 894 (1992) (month of references unknown).

Riv.Ital. 56, 567 (1974).

B. Brang, "Development and Trends of Sugar Derived Surfactants", Seifen–Öle–Fette–Wachse 118, 905 (Jan. 15, 1992).

Bull. Soc. Chim. France, 333 (1949) (month of reference unknown).

*Primary Examiner*—Richard D. Lovering
*Assistant Examiner*—Daniel S. Metzmaier
*Attorney, Agent, or Firm*—Wayne C. Jaeschke; John E. Drach; Henry E. Millson, Jr.

[57] ABSTRACT

Foaming emulsions comprising:
(A) oily mixture comprising fatty alcohols polyglycol ethers, Guerbet alcohols, and fatty acid esters selected from the group consisting of:
  (a) a fatty ester of formula III, $$R^2CO\text{—}OR^3 \qquad (III)$$

wherein $R^2CO$ is an aliphatic acyl radical containing 6 to 22 carbon atoms and 0, 1, 2 or 3 double bonds and $R^3$ is a linear or branched alkyl radical containing 1 to 4 carbon atoms, and
  (b) a polyol partial ester of glycerol, oligoglycerol or oligoglycerol polyglycol ether with fatty acids containing 12 to 22 carbon atoms; dialkyl ethers and paraffin hydrocarbons,
(B) fatty alcohol sulphates and/or fatty alcohol polyglycol ether sulphates,
(C) an anionic polymer,
(D) an alkyl oligoglycosides,
(E) a cationic surfactant or polymers,
(F) an electrolytic salt, and
(G) water.

These emulsions have a cosmetically elegant appearance and are suitable for example for producing two-in-one shower baths.

17 Claims, No Drawings

FOAMING EMULSIONS

This application is filed under 35 U.S.C. 371 of PCT/EP94/00098, filed Jan. 14, 1994, published as WO94/16668, Aug. 4, 1994.

BACKGROUND OF THE INVENTION

1. Field of the Invention

This invention relates to foaming emulsions based on alkyl oligoglycosides, to a process for their production, in which a pre-emulsion is prepared from an oil phase and a polymer phase and a surfactant phase is stirred into the pre-emulsion thus formed, to shower baths containing these emulsions and to the use of the emulsions for the production of hair-care and body-care products.

2. Statement of Related Art

Alkyl oligoglycosides are nonionic surfactants which are distinguished not only by favorable foaming and cleaning power, but also and in particular by ready biodegradability and particularly advantageous dermatological compatibility. Accordingly, this class of surface-active compounds is acquiring increasing significance for the manufacture of cosmetic products. Relevant synoptic articles have been published, for example, by D. Balzer et al. in Tens. Surf. Det. 28, 419 (1991) and Seifen-Öle-Fette-Wachse 118, 894 (1992).

Alkyl oligoglycosides and, in particular, alkyl oligoglucosides are known in principle as ingredients of a number of cosmetic products.

Formulations containing sulfosuccinates in addition to short-chain alkyl oligoglucosides, for example for hair shampoos and shower baths, are disclosed in Riv. Ital. 56, 567 (1974).

Foaming detergent mixtures containing a number of anionic, nonionic and amphoteric surfactants in addition to alkyl oligoglucosides are known, for example, from EP-B-0 070 074, EP-B-0 070 075, EP-B-0 070 076 and EP-B-0 070 077 (Procter & Gamble).

In addition, mixtures of alkyl oligoglucosides with alkyl (ether) phosphates [1], cationic polymers [2], monoalkyl sulfosuccinates [3], silicone compounds [4] and sugar esters [5], which may be used for cosmetic purposes, are also known (for [1], see EP-A-0 324 451; for [2], see EP-A-0 337 354; for [3], see EP-A-0 358 216; for [4] see EP-A-0 398 117 and for [5] see EP-A-0 409 005, all Kao). DE-B-41 29 926 (Kao) relates to tinting shampoos which may contain sulfosuccinates, sarcosinates and amine oxides in addition to alkyl oligoglucosides.

EP-A-0 384 983 and EP-A-0 490 041 (Hüls) describe shower baths and hair shampoos containing ether carboxylic acids and electrolyte salts or sulfate surfactants in addition to alkyl oligoglucosides. The use of mixtures containing alkyl oligoglucosides, polymers and salts as thickeners for surfactants in cosmetics is proposed in DE-A-41 14 141 (Hüls).

DE-A-36 40 755 (Henkel) relates to aqueous, free-flowing pearlescent concentrates containing mixtures of alkyl oligoglucosides and polyethylene glycol esters or fatty acid alkanolamides. DE-A-40 33 928 (Henkel) describes oil-in-water emulsions containing oils, fatty acid partial glycerides and saturated alcohols in addition to alkyl oligoglucosides.

In addition, shampoos containing octyl decyl glucoside, collagen derivatives and polymers are known from an article by B. Brancq in Seifen-Öle-Fette-Wachse 118, 905 (1992).

Finally, formulations of $C_{8/10}$ alkyl glucoside and sulfosuccinates are disclosed in the same article.

However, there is still a growing need in the field of hair-care and body-care products for particularly mild formulations which combine aspects of cleaning and care with one another in addition to showing good dermatological compatibility. A typical example of such formulations are so-called "two-in-one" shower or foam baths which simultaneously cleanse and cream the skin.

Although products of the type in question are known in principle, they are often unsatisfactory from the point of view of practical application. The emulsions lack cosmetic elegance, i.e. they gel and are not readily absorbed by the skin and, instead of a creamy microfoam, they only form a coarse macrofoam. The production of stable emulsions of the type mentioned which do not separate in the event of prolonged storage has also proved to be difficult in the past and requires a complicated technique for homogenization.

Accordingly, the problem addressed by the present invention was to provide new foaming emulsions which would be free from the described disadvantages.

DESCRIPTION OF THE INVENTION

The present invention relates to foaming emulsions containing

A) oils selected from the group consisting of fatty alcohol polyglycol ethers, Guerbet alcohols, fatty acid alkyl esters, polyol partial esters, dialkyl ethers and paraffin hydrocarbons, B) anionic and/or nonionic polymers, C) fatty alcohol sulfates and/or fatty alcohol polyglycol ether sulfates, D) alkyl oligoglycosides, E) cationic surfactants or polymers, F) electrolyte salts and G) water.

It has surprisingly been found that the emulsions according to the invention show high cosmetic elegance, i.e. they develop a creamy consistency and are easily absorbed by the skin. In addition, they form a rich and creamy microfoam. The emulsions according to the invention have high cleansing power and combine this with surprising refatting power so that, for example, there is virtually no need to apply a skin cream.

Foaming emulsions with the following composition have proved to be particularly advantageous:

1 to 5% by weight of fatty alcohol polyglycol ethers, 1 to 5% by weight of Guerbet alcohols, 1 to 5% by weight of polyol partial esters, 1 to 5% by weight of anionic polymers, 15 to 30% by weight of fatty alcohol polyglycol ether sulfates, 15 to 30% by weight of alkyl oligoglycosides, 0.1 to 10% by weight of cationic surfactants or polymers, 0.1 to 3% by weight of electrolyte salts and ad 100% by weight of water.

The present invention also relates to a process for the production of foaming emulsions in which a pre-emulsion is formed from an oil phase I containing a1) fatty alcohol polyglycol ethers, a2) Guerbet alcohols, a3) fatty acid esters, a4) polyol partial esters, a5) dialkyl ethers and/or a6) paraffin hydrocarbons and an aqueous polymer phase II and an aqueous phase III containing c1) fatty alcohol sulfates, c2) fatty alcohol polyglycol ether sulfates, c3) alkyl oligoglycosides, c4) cationic surfactants or polymers and/or c5) electrolyte salts is incorporated at 50° to 70° C. in the pre-emulsion thus formed.

It has surprisingly been found that emulsions remaining stable in storage for long periods can be obtained by the process according to the invention. Extensive tests in this regard have shown that both the stability in storage and also the appearance of the emulsions are very closely linked to the composition of the three phases and to the sequence of the production steps.

Ingredients of the Oil Phase I

Low-spreading and medium-spreading oils may be used as ingredients for the oil phase which are responsible for the refatting properties of the emulsions according to the invention. A combination of the three components a1), a2) and a4) has proved to be particularly advantageous.

Fatty alcohol polyglycol ethers corresponding to formula (I):

$$R^1O—(CH_2CH_2O)_xH \qquad (I)$$

in which $R^1$ is an alkyl radical containing 12 to 22 carbon atoms and x is a number of 5 to 30, may be used as component a1).

Typical examples are adducts of, on average, 5 to 30 and preferably 10 to 25 moles of ethylene oxide with lauryl alcohol, myristyl alcohol, cetyl alcohol, stearyl alcohol, isostearyl alcohol, arachyl alcohol and behenyl alcohol and the technical mixtures thereof obtained, for example, in the high-pressure hydrogenation of methyl ester fractions or aldehydes from Roelen's oxo synthesis. It is particularly preferred to use an adduct of around 20 moles of ethylene oxide with technical cetostearyl alcohol.

Guerbet alcohols corresponding to formula (II):

$$\begin{array}{c}CH_2OH \\ | \\ CH_3CH_2(CH_2)_yCH—(CH_2)_{y-2}CH_2CH_3\end{array} \qquad (II)$$

in which y is a number of 6 to 12, may be used as component a2).

The alcohols in question are primary, branched alcohols which are prepared in known manner by base-catalyzed dimerization of fatty alcohols. Typical examples are 2-hexyl decanol, 2-octyl dodecanol and 2-decyl tetradecanol.

The fatty acid esters of component a3) are understood to be compounds corresponding to formula (III):

$$R^2CO—OR^3 \qquad (III)$$

in which $R^2CO$ is an aliphatic acyl radical containing 6 to 22 carbon atoms and 0, 1, 2 or 3 double bonds and $R^3$ is a linear or branched alkyl radical containing 1 to 4 carbon atoms. Typical examples are ethyl, propyl, butyl and, in particular, methyl esters of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils or as monomer fraction in the dimerization of unsaturated fatty acids. $C_{16/18}$ fatty acid methyl esters are preferably used.

The compounds of component a4) are polyol partial esters, more precisely esters of glycerol or oligoglycerol or oligoglycerol polyglycol ethers with fatty acids containing 12 to 22 carbon atoms. Besides glycerol, technical oligoglycerol mixtures with a degree of auto-condensation of, on average, 2 to 10 and preferably 2 to 5 and adducts of, on average, 1 to 10 and preferably 2 to 5 moles of ethylene oxide with these oligoglycerols are particularly suitable polyol components. The fatty acid component may be selected from lauric acid, myristic acid, palmitic acid, stearic acid, isostearic acid, oleic acid, ricinoleic acid and behenic acid and technical mixtures thereof. Typical examples of polyol partial esters which may be used in accordance with the invention are partial esters of diglycerol and diglycerol 2EO adduct with stearic acid.

Suitable dialkyl ethers (component a5) are compounds corresponding to formula (IV):

$$R^4—O—R^5 \qquad (IV)$$

in which $R^4$ and $R^5$ independently of one another represent alkyl radicals containing 6 to 22 carbon atoms.

The compounds in question are known compounds which may be obtained by the relevant methods of preparative organic chemistry. Processes for their production, for example by condensation of fatty alcohols in the presence of p-toluene sulfonic acid, are known, for example, from Bull. Soc. Chim. France, 333 (1949), DE-A1 40 39 950 (Hoechst) and DE-A1 41 03 489 (Henkel). Symmetrical dialkyl ethers containing 6 to 12 carbon atoms in the alkyl radicals are preferred from the applicational point of view. Dialkyl ethers corresponding to formula (IV), in which $R^4$ and $R^5$ are octyl and/or 2-ethylhexyl radicals, spread particularly quickly. Accordingly, particularly preferred dialkyl ethers for the purposes of the invention are di-n-octyl ether and di-2-ethylhexyl ether.

Finally, paraffin hydrocarbons (component a6) are known technical alkane mixtures which are typically used as oils in cosmetic products. The paraffins in question are preferably low-viscosity paraffins with a density of 0.81 to 0.875.

The percentage content of ingredients of the oil phase in the emulsion as a whole may vary within the following limits:

a1) 1 to 5% by weight and preferably 1 to 2% by weight;

a2) 1 to 5% by weight and preferably 2 to 4% by weight;

a3) 1 to 5% by weight and preferably 2 to 4% by weight;

a4) 1 to 5% by weight and preferably 2 to 4% by weight;

a5) 1 to 5% by weight and preferably 2 to 4% by weight;

a6) 1 to 5% by weight and preferably 2 to 4% by weight.

The percentage content of oil phase in the emulsion according to the invention may be from 6 to 30% by weight and is preferably from 11 to 22% by weight, based on the emulsion. Another surprising effect is that, despite this oil content, the emulsions according to the invention still show pronounced foaming power.

Ingredients of the Polymer Phase II

The aqueous polymer phase critically determines the appearance of the emulsions according to the invention. Suitable ingredients are anionic and/or nonionic polymers.

Aqueous anionic polystyrene dispersions of the type known in principle for the production of cosmetic preparations have proved to be particularly suitable.

Nonionic polymers of the polyethylene glycol mono/difatty acid ester type with a degree of condensation of 2 to 100 and preferably 10 to 100 are also suitable. A typical example is polyethylene glycol-100-bis-stearate which provides the emulsions with an additional pearlescent effect.

The polymers may be used individually or in combination in quantities of 1 to 5% by weight and preferably 2 to 4% by weight, based on the emulsion. They are introduced into the pre-emulsion in the form of aqueous dispersions, i.e. the main quantity of water to be present in the final formulation is introduced together with the polymers. This quantity is normally between 15 and 66% by weight and preferably between 35 and 55% by weight, based on the emulsion.

Ingredients of the Surfactant Phase III

The surfactant phase which is added to the pre-emulsion formed from phases I and II is responsible for the cleansing effect of the emulsion. A combination of components c2) and c3), to which cationic surfactants or polymers (component c4) and small quantities of electrolyte salts (component c5) may be added for foam structuring and for viscosity adjustment, respectively, has proved to be particularly advantageous.

In this connection, component c1) may be selected from fatty alcohol sulfates corresponding to formula (V):

$$R^6O\text{---}SO_3X \qquad (V)$$

in which $R^6$ represents $C_{12-14}$ alkyl radicals and X is an alkali metal and/or alkaline earth metal, ammonium or alkylammonium.

Typical examples are sulfates of lauryl alcohol, myristyl alcohol, cetyl alcohol, stearyl alcohol, isostearyl alcohol, arachyl alcohol, behenyl alcohol and the technical mixtures thereof formed, for example, in the high-pressure hydrogenation of methyl ester fractions or aldehydes from Roelen's oxo synthesis. Sulfates of $C_{12/14}$ or $C_{12/18}$ cocofatty alcohol are preferably used in the form of their sodium and/or magnesium salts.

Component c2) may be selected from fatty alcohol polyglycol ether sulfates corresponding to formula (VI):

$$R^7O\text{---}(CH_2CH_2O)_zSO_3X \qquad (VI)$$

in which $R^7$ represents $C_{12-14}$ alkyl radicals, z is a number of 1 to 10 and X is an alkali metal and/or alkaline earth metal, ammonium or alkylammonium.

Typical examples are sulfates of adducts of, on average, 1 to 10 and preferably 2 to 7 moles of ethylene oxide with lauryl alcohol, myristyl alcohol, cetyl alcohol, stearyl alcohol, isostearyl alcohol, arachyl alcohol, behenyl alcohol and the technical mixtures thereof obtained, for example, in the high-pressure hydrogenation of methyl ester fractions or aldehydes from Roelen's oxo synthesis. Sulfates of an adduct of, on average, 2 to 4 moles of ethylene oxide with $C_{12/14}$ or $C_{12/18}$ cocofatty alcohol in the form of their sodium and/or magnesium salts are preferably used. The fatty alcohol polyglycol ether sulfates may have a conventional or narrow homolog distribution. It is pointed out that fatty alcohol polyglycol ether sulfates with a conventional homolog distribution and a low degree of alkoxylation may advantageously contain significant amounts of fatty alcohol sulfates from their production.

Component c3) may be selected from alkyl oligoglycosides corresponding to formula (VII):

$$R^8\text{---}O\text{---}[G]_p \qquad (VII)$$

in which $R^8$ is a $C_{6-22}$ alkyl radical, G is a sugar unit containing 5 to 6 carbon atoms and p is a number of 1 to 10.

As mentioned above, the alkyl oligoglycosides are known substances which may be obtained by the relevant methods of preparative organic chemistry. EP-A1-0 301 298 and WO 90/3977 are cited as representative of the extensive literature available on the subject. The alkyl oligoglycosides may be derived from aldoses or ketoses containing 5 or 6 carbon atoms, preferably glucose. Accordingly, the preferred alkyl oligoglycosides are alkyl oligoglucosides.

The index p in general formula (VII) indicates the degree of oligomerization (DP degree), i.e. the distribution of monoglycosides and oligoglycosides, and is a number of 1 to 10. Whereas p is a given compound must always be an integer and, above all, may assume a value of 1 to 6, the value p for a certain alkyl oligoglycoside is an analytically determined calculated quantity which is generally a broken number. Alkyl oligoglycosides with an average degree of oligomerization p of 1.1 to 3.0 are preferably used. Alkyl oligoglycosides with a degree of oligomerization of less than 1.7 and, more particularly, from 1.2 to 1.4 are preferred from the applicational point of view.

The alkyl radical $R^8$ may be derived from primary alcohols containing 6 to 11 and preferably 8 to 10 carbon atoms. Typical examples are caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxo synthesis. Preferred alkyl oligoglucosides are those with a chain length of $C_{8-10}$ (DP=1 to 3) which are obtained as first runnings in the removal of technical $C_{8-18}$ cocofatty alcohol by distillation and which may contain less than 6% by weight of $C_{12}$ alcohol as an impurity, and also alkyl oligoglucosides based on technical $C_{9/11}$ oxoalcohols (DP=1 to 3).

The alkyl radical $R^8$ may also be derived from primary alcohols containing 12 to 22 and preferably 12 to 16 carbon atoms. Typical examples are lauryl alcohol, myristyl alcohol, cetyl alcohol, stearyl alcohol, isostearyl alcohol, arachyl alcohol, behenyl alcohol and the technical mixtures thereof obtainable as described above. Alkyl oligoglucosides based on hydrogenated $C_{12/16}$ cocoalcohol with a DP of 1 to 3 are preferred.

Cationic surfactants or polymers (component c4) are suitable for foam structuring.

Cationic surfactants in this context are quaternary ammonium compounds such as, for example, N-(2-hydroxyhexadecyl)-N,N-dimethyl-N-2-hydroxyethyl ammonium chloride (Dehyquart® E, a product of Henkel KGaA, Düsseldorf/FRG) or esterquats such as, for example, methylquaternized triethanolamine mono/distearate dimethyl sulfate salt (Dehyquart® AU 36, a product of Pulcra S. A., Barcelona/ES).

Cationic polymers are, for example, cationic cellulose derivatives, cationic starch derivatives, copolymers of diallyl QUATS with acrylamides, quaternized polyvinyl pyrrolidone derivatives, quaternized vinyl pyrrolidone/vinyl imidazole polymers (Luviquats, BASF AG, Ludwigshafen/FRG), polyglycol amine condensates, quaternized collagen polypeptides, polyethylene imines, cationic silicone polymers (Amodimethicones), copolymers of adipic acid with dimethylaminohydroxypropyl diethylenetriamine (Cartaretines), polyaminopolyamides, cationic chitin derivatives, quaternized ammonium salt polymers (Mirapols) and, in particular, cationic guar gum (Cosmedia Guar).

Electrolyte salts (component c5) are used for viscosity adjustment, chlorides of the alkali metals and/or alkaline earth metals being suitable. Sodium chloride and/or magnesium chloride are normally used.

The percentage content of ingredients of the surfactant phase in the emulsion as a whole may vary within the following limits:

c1) 0 to 10% by weight and preferably 1 to 5% by weight c2) 15 to 30% by weight and preferably 20 to 25% by weight;

c3) 15 to 30% by weight and preferably 15 to 20% by weight;

c4) 0.1 to 10% by weight and preferably 0.1 to 5% by weight;

c5) 0.1 to 3% by weight and preferably 1 to 2% by weight.

It follows from this that the percentage content of surfactant phase in the emulsions according to the invention may be from 30 to 83% by weight and preferably from 37 to 57% by weight, based on the emulsion. The surfactants are normally used in the form of more or less concentrated aqueous pastes or solutions, so that a further quantity of water, albeit smaller by comparison with the polymer phase, may be introduced into the emulsions according to the invention with the surfactant phase.

Preparation of the Emulsions

A simple stirrer-equipped apparatus is sufficient for the preparation of the emulsions. Surprisingly, the usual technique, in which homogenization is carried out with intensive shearing, for example in an Ultra-Turrax or in a colloid mill, is not necessary although it may of course be carried out in such an apparatus.

It has proved to be optimal initially to heat the oil phase and the aqueous polymer phase to a temperature of 70° to 90° C. and preferably 75° to 80° C. and then to mix the two phases at that temperature to form a pre-emulsion. The cold surfactant phase, i.e. the surfactant phase at ambient temperature, may then be stirred into the pre-emulsion at 50° to 70° C. and preferably at 60° to 65° C.

Formation of the emulsion is a purely mechanical or physical process which does not involve a chemical reaction.

Commercial Applications

The foaming emulsions according to the invention combine cleansing and care properties and are particularly suitable for applications in the cosmetics field.

The present invention also relates to shower baths based on foaming emulsions containing A) oils selected from the group consisting of fatty alcohol polyglycol ethers, Guerbet alcohols, fatty acid esters, polyol partial esters, dialkyl ethers and paraffin hydrocarbons, B) anionic and/or nonionic polymers, C) fatty alcohol sulfates and/or fatty alcohol polyglycol ether sulfates, D) alkyl oligoglycosides, E) cationic surfactants or polymers, F) electrolyte salts and G) water and optionally other typical auxiliaries and additives.

Finally, the present invention relates to the use of the foaming emulsions according to the invention for the production of hair-care and body-care products in which they may be present in quantities of 1 to 100% by weight and preferably 50 to 95% by weight, based on the particular product.

The following Examples are intended to illustrate the invention without limiting it in any way.

EXAMPLES

Ingredients used

Eumulgin® B2 cetyl stearyl alcohol containing approx. 20 moles of ethylene oxide Eutanol® G 2-octyl dodecanol Lamecreme® DGE 18 oligoglycerol 2EO tetrastearate Lytron® 631 anionic polystyrene dispersion Texapon® N70 $C_{12/14}$ cocofatty alcohol 2EO sulfate sodium salt Dehyton® G hydroxyethyl-N-cocoamidoethyl carboxymethyl glycinate sodium salt Plantaren® 1200 $C_{12/14}$ alkyl oligoglucoside II. Formulation Examples Example 1

Phase I: 20 g (1% by weight) Eumulgin® B2

60 g (3% by weight) Eutanol® G 80 g (4% by weight) Lamecreme® DGE 18

Phase II: 40 g (2% by weight) Lytron® 631

980 g (49% by weight) water

Phase III: 440 g (22% by weight) Texapon® N70

320 g (16% by weight) Plantaren® APG 1200

20 g (1% by weight) sodium chloride 40 g (2% by weight) water

In a 3 liter stirred apparatus, 160 g of phase I were stirred with 1020 g of phase II at 70° C. to form a pre-emulsion. 820 g of cold phase III were then stirred in at 60° C. A free-flowing, fine-particle, smooth emulsion forming a creamy foam was obtained and was rapidly absorbed by the skin.

Comparison Example C1

Phase I: 20 g (1% by weight) Eumulgin® B2

60 g (3% by weight) Eutanol® G 80 g (4% by weight) Lamecreme® DGE 18

Phase II: 40 g (2% by weight) Lytron® 631

720 g (36% by weight) water

Phase III: 540 g (27% by weight) Texapon® N70

320 g (16% by weight) Dehyton® G 20 g (1% by weight) sodium chloride 200 g (10% by weight) water As in Example 1, 160 g of phase I were stirred at 80° C. with 760 g of phase II to form a pre-emulsion. 1080 g of cold phase III were then stirred in at 60° C. The emulsion obtained showed unfavorable gel-like flow behavior by comparison with Example 1 and had lower foaming power. In addition, the emulsion was difficult to spread on the skin.

Comparison Example C2

Phase I: 20 g (1% by weight) Eumulgin® B2

60 g (3% by weight) Eutanol® G 80 g (4% by weight) Lamecreme® DGE 18

Phase II: 40 g (2% by weight) Lytron® 631

980 g (49% by weight) water

Phase III: 440 g (22% by weight) TexaPon® N70

320 g (16% by weight) Dehyton® G 20 g (1% by weight) sodium chloride 40 g (2% by weight) water In a 3 liter stirred apparatus, 160 g of phase I were stirred at 80° C. with 1020 g of phase II to form a pre-emulsion. 820 g of cold phase III were then stirred in at 60° C. The emulsion obtained showed unfavorable gel-like flow behavior by comparison with Example 1 and had lower foaming power. Similarly to C1, the emulsion was difficult to spread on the skin.

What is claimed is:

1. A foaming emulsion comprising:
   (A) an oil mixture comprising a fatty alcohol polyglycol ether, a Guerbet alcohol, and a fatty acid ester selected from the group consisting of
      (a) a fatty acid ester of formula III $$R^2CO-OR^3 \quad (III)$$

wherein $R^2CO$ is an aliphatic acyl radical containing 6 to 22 carbon atoms and 0, 1, 2 or 3 double bonds and $R^3$ is a linear or branched alkyl radical containing 1 to 4 carbon atoms, and
      (b) a polyol partial ester of glycerol, oligoglycerol or oligoglycerol polyglycol ether with fatty acids containing 12 to 22 carbon atoms;
   (B) at least one of a fatty alcohol sulfate and a fatty alcohol polyglycol ether sulfate;
   (C) an anionic polymer other than a fatty alcohol polyglycol ether sulfate;
   (D) an alkyl oligoglycoside;
   (E) a cationic surfactant or polymer;
   (F) an electrolyte salt; and
   (G) water.

2. The emulsion of claim 1 wherein a component (A) also contains at least one of a dialkyl ether and a paraffin hydrocarbon.

3. The emulsion of claim 1 wherein the fatty acid ester of component (A) is a polyol partial ester (b).

4. The emulsion of claim 1 wherein the emulsion contains from about 1 to about 5% by weight of fatty alcohol polyglycol ether, from about 1 to about 5% by weight of a Guerbet alcohol, from about 1 to about 5% by weight of polyol partial ester, from about 15 to about 30% by weight of fatty alcohol polyglycol ether sulfate, from about 1 to about 5% by weight of component (C), from about 15 to about 30% by weight of component (D), from about 0.1 to about 10% by weight of component (E), from about 0.1 to about 3% by weight of component (F), and the remainder component (G).

5. The emulsion of claim 1 wherein component (E) is a quaternary ammonium compound or an esterquat.

6. The emulsion of claim 1 wherein component (E) is cationic guar gum.

7. The emulsion of claim 1 wherein in component (A) the fatty alcohol polyglycol ether has the formula:

$$R^1O-(CH_2CH_2O)_xH \quad (I)$$

wherein $R^1$ is an alkyl radical containing 12 to 22 carbon atoms and x is a number of 5 to 30.

8. The emulsion of claim 1 wherein in component (A) the Guerbet alcohol has the formula $$\begin{array}{c} CH_2OH \\ | \\ CH_3CH_2(CH_2)_yCH-(CH_2)_{y-2}CH_2CH_3 \end{array} \quad (II)$$

wherein y is a number of 6 to 12.

9. The emulsion of claim 1 wherein component (C) is an anionic polystyrene dispersion.

10. The emulsion of claim 1 wherein component (B) is selected from the group consisting of a fatty alcohol sulfate of the formula:

$$R^6O-SO_3X \quad (V)$$

wherein $R^6$ is a $C_{12-14}$ alkyl radical and X is an alkali metal, alkaline earth metal, ammonium or alkylammonium ion, and a fatty alcohol polyglycol ether sulfate of the formula:

$$R^7O-(CH_2CH_2O)_zSO_3X \quad (VI)$$

wherein $R^7$ is a $C_{12-14}$ alkyl radical, z is a number of 1 to 10 and X is an alkali metal, alkaline earth metal, ammonium or alkylammonium ion.

11. The emulsion of claim 1 wherein component (D) is a compound of the formula:

$$R^8-O-(G)_p \quad (VII)$$

wherein $R^8$ is a $C_{6-22}$ alkyl radical, G is a sugar unit containing 5 to 6 carbon atoms and p is a number of 1 to 10.

12. A process for the production of a foaming emulsion comprising the steps of
   (I) forming an oil phase comprising a fatty alcohol polyglycol ether, a Guerbet alcohol, and a fatty acid ester selected from the group consisting of
      (a) a fatty acid ester of formula III $$R^2CO-OR^3 \quad (III)$$

wherein $R^2CO$ is an aliphatic acyl radical containing 6 to 22 carbon atoms and 0, 1, 2 or 3 double bonds and $R^3$ is a linear or branched alkyl radical containing 1 to 4 carbon atoms, and
      (b) a polyol partial ester of glycerol, oligoglycerol or oligoglycerol polyglycol ether with fatty acids containing 12 to 22 carbon atoms;
   (II) forming an aqueous polymer phase comprising (a) an anionic polymer other than a fatty alcohol polyglycol ether sulfate, and (b) an electrolyte salt;
   (III) forming a surfactant phase comprising (a) at least one of a fatty alcohol sulfate and a fatty alcohol polyglycol ether sulfate, (b) an alkyl oligoglycoside, and (c) a cationic surfactant or polymer;
   (IV) heating phase (I) and phase (II) to a temperature in the range of from about 70 to about 90° C.;
   (V) mixing heated phases (I) and (II) together to form a pre-emulsion; and
   (VI) mixing phase (III) with said pre-emulsion to form the foaming emulsion.

13. The process of claim 12 wherein step (IV) is carried out at a temperature in the range of from about 75° to about 80° C.

14. The process of claim 12 wherein in step (VI) phase III is stirred into the pre-emulsion at a temperature in the range of from about 50° to about 70° C.

15. The process of claim 12 wherein said fatty alcohol polyglycol ether is a compound of the formula (I):

$$R^1O-(CH_2CH_2O)_xH \quad (I)$$

wherein $R^1$ is an alkyl radical containing 12 to 22 carbon atoms and x is a number of 5 to 30; said Guerbet alcohol is a compound of the formula (II):

$$\begin{array}{c} CH_2OH \\ | \\ CH_3CH_2(CH_2)_yCH-(CH_2)_{y-2}CH_2CH_3 \end{array} \quad (II)$$

wherein y is a number of 6 to 12; said surfactant phase (III) contains at least one of a fatty alcohol sulfate of the formula (V):

$$R^6O-SO_3X \quad (V)$$

wherein $R^6$ is a $C_{12-14}$ alkyl radical and X is an alkali metal, alkaline earth metal, ammonium or alkylammonium ion, and a fatty alcohol polyglycol ether sulfate of the formula (VI):

$$R^7O-(CH_2CH_2O)_zSO_3X \quad (VI)$$

wherein $R^7$ is a $C_{12-14}$ alkyl radical, z is a number of 1 to 10 and X is an alkali metal, alkaline earth metal, ammonium or alkylammonium ion; and said alkyl oligoglycoside is a compound of the formula (VII):

$$R^8-O-(G)_p \quad (VII)$$

wherein $R^8$ is a $C_{6-22}$ alkyl radical, G is a sugar unit containing 5 to 6 carbon atoms and p is a number of 1 to 10.

16. The process of claim 12 wherein said cationic surfactant is a quaternary ammonium compound or an esterquat.

17. The process of claim 12 wherein said cationic polymer is cationic guar gum.

* * * * *